(12) United States Patent
Puschett

(10) Patent No.: US 7,759,329 B2
(45) Date of Patent: *Jul. 20, 2010

(54) METHOD OF TREATING HUMAN PREECLAMPSIA EMPLOYING RESIBUFAGENIN

(75) Inventor: Jules B. Puschett, Belton, TX (US)

(73) Assignee: The Administrators of the Tulane Educational Fund, New Orleans, LA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/577,450

(22) PCT Filed: Sep. 23, 2005

(86) PCT No.: PCT/US2005/034075

§ 371 (c)(1), (2), (4) Date: Jan. 22, 2008

(87) PCT Pub. No.: WO2006/044107

PCT Pub. Date: Apr. 27, 2006

(65) Prior Publication Data

US 2008/0261928 A1    Oct. 23, 2008

Related U.S. Application Data

(60) Provisional application No. 60/619,969, filed on Oct. 19, 2004.

(51) Int. Cl.
*A61K 31/56* (2006.01)
*A61K 31/58* (2006.01)
*A01N 45/00* (2006.01)

(52) U.S. Cl. .......................... 514/170; 514/172; 514/26; 514/25; 536/4.1

(58) Field of Classification Search .................. 514/26, 514/25, 170, 172; 536/4.1
See application file for complete search history.

(56) References Cited

U.S. PATENT DOCUMENTS 3,585,187 A    6/1971  Heider et al.
5,770,376 A    6/1998  Bagrov
6,306,845 B1  10/2001  Butler, Jr.

FOREIGN PATENT DOCUMENTS

JP           57056500 A  *  4/1982

OTHER PUBLICATIONS

Derwent abstract of Fukuyama et al.; JP 57056500 A; Apr. 5, 1982.*
Poster Session: Preeclampsia II (Friday, Mar. 26, 2004, 9:30 a.m.-11:30 a.m.), J Soc Gynecol Investig vol. 11, No. 2 (Supplement), Feb. 2004, 2 pp.
Basic Hypertension II, Journal of the American Society of Nephrology, vol. 13, Sep. 2002, Program and Abstracts Issue, 3 pp.
Biochemical and biophysical Research Communications, vol. 143, No. 1, Feb. 27, 1987, Academic Press, Inc. Harcourt Brace Jovanovich, Publishers, 9 pp.
Lopatin et al., "Circulating bufodienolide and cardenolide sodium pump inhibitors in preeclampsia", Journal of Hypertension, vol. 17, No. 8, Aug. 1999, pp. 1179-1187.
Hayman et al., "Plasma from women with pre-eclampsia induces an in vitro alteration in the endothelium-dependent behaviour of myometrial resistance arteries", BJOG, An International Journal of Obstetrics and Gynaecology, vol. 107, No. 1, Jan. 2000, Edited by John M. Grant, pp. 108-115.
Graves, Steven W., "The Possible Role of Digitalislike Factors in Pregnancy-Induced Hypertension", Hypertension Supplement, Workshop on Cation Transport and Natriuretic Factors, vol. 10, No. 5, Nov. 1987, pp. I-84 to I-86.

* cited by examiner

*Primary Examiner*—Shaojia Anna Jiang
*Assistant Examiner*—Michael C Henry
(74) *Attorney, Agent, or Firm*—Eckert Seamans Cherin & Mellott, LLC; Arnold B. Silverman, Esq.

(57) ABSTRACT

A method of treating preeclampsia including administering a therapeutically effective dose of resibufagenin to a patient having preeclampsia. Effecting the determination of the presence of preeclampsia may be by determining whether there has been a substantial elevation in marinobufagenin which may be blood-derived or urine-derived and if such elevation does exist, concluding that preeclampsia does exist. The method may advantageously be practiced by employing urine, blood serum or blood plasma as the body specimen containing the protein in determining whether a patient has preeclampsia. In another embodiment, bufodienolide derivatives other than resibufagenin may be employed in lieu of thereof or in combination therewith. In another embodiment, resibufagenin analogues may be employed in the treatment of preeclampsia.

11 Claims, No Drawings

METHOD OF TREATING HUMAN PREECLAMPSIA EMPLOYING RESIBUFAGENIN

This application is a 371 of PCT/US05/34075 filed Sep. 23, 2005 which claims benefit of the U.S. Provision Application No. 60/619,969 filed Oct. 19, 2004.

BACKGROUND OF THE INVENTION

1. Field of the Invention

The present invention provides a method for treating a patient that has preeclampsia and, more specifically, it provides such a method which employs resibufagenin in treating preeclampsia.

2. Description of the Prior Art

Eclampsia, which is a condition experienced by pregnant women, and generally involves coma and/or convulsive seizures during the same period without other etiology. Preeclampsia, if untreated, can progress suddenly to eclampsia which is usually fatal if untreated.

Preeclampsia is generally characterized by the presence of hypertension proteinuria and edema. It is a disorder which generally occurs only in women who are more than 20 weeks pregnant.

Elevated blood pressure or hypertension has long been recognized as a health problem. It is a very common disease which can have widespread effects on a patient's body and frequently, unlike numerous other diseases, is asymptomatic.

Despite known means of measuring blood pressure of a patient as by a sphygmomanometer, for example, there is lacking an accurate reliable means of detecting the presence of volume dependent hypertension involving higher arterial blood pressure by use of a body specimen, such as blood serum or blood plasma.

From a pathogenetic standpoint, essential hypertension may be divided into two broad categories: (a) volume expansion hypertension, and (b) vasoconstriction hypertension. It has been estimated that about 30 to 40 percent of human essential hypertension may be etiologically related to volume expansion hypertension, especially in certain demographic groups. Previous studies participated in by the present inventor have demonstrated an alteration in the phosphorylation of a proximal tubular membrane protein following acute saline expansion of the experimental rat (Puschett et al. Volume Expansion Induced Changes in Renal Tubular Membrane Protein Phosphorylation, Biochem. Biophys. Res. Commun., 143:pp. 74-80 (1987)).

U.S. Pat. No. 5,770,376 discloses the use of a blood or urine specimen in diagnosing hypertension as an indication of acute myocardial infarction. It employs plasma and/or levels of a marinobufagenin-like immunoreactivity as a marker for hypertension.

U.S. patent application Ser. No. 10/109,203 discloses a substantial reduction in phosphorylation or concentration of a specific protein obtained from a body specimen to determine the presence of preeclampsia.

Abandoned U.S. patent application Ser. No. 09/990,432, filed Nov. 21, 2001, in the name of the present inventor, the disclosure of which is expressly incorporated herein by reference, discloses the use of the CLAMP protein in effecting a determination of the presence of chronic volume dependent hypertension.

U.S. Patent Application Ser. No. 60/444,730, filed Feb. 4, 2003, in the name of the present inventor, the disclosure of which is expressly incorporated herein by reference, discloses the use of elevation of marinobufagenin in a body specimen of a pregnant woman to determine whether the patent has preeclampsia.

While there is no hard and fast rule regarding diagnosis of preeclampsia, several standards have been applied. If a pregnant woman develops a blood pressure of 140/90, and has edema of the face or hands, and the presence of urinary protein in concentrations greater than 0.3 grams in a 24 hour urine collection, this is generally indicative of the presence of preeclampsia.

There remains, therefore, a very real and substantial need for a method for effectively treating preeclampsia in a pregnant patient.

SUMMARY OF THE INVENTION

The present invention has met the above-described need by providing a method of treating preeclampsia in a patient which may be a human patient.

Prior to treatment, the determination of the presence of preeclampsia in a patient may involve determining whether there is a substantial elevation in marinobufagenin in blood-derived or urine-derived specimens and, if such elevation does exist, concluding that preeclampsia exists.

A therapeutically effective dosage of resibufagenin may be administered orally or parenterally.

It is an object of the present invention to provide a method for effectively preventing or treating human preeclampsia in a reliable and rapid manner.

It is yet another object of the present invention to employ resibufagenin in the treatment of human preeclampsia.

It is a further object of the present invention to determine the presence of preeclampsia by the elevation in marinobufagenin in a body specimen of a pregnant woman followed by subsequent treatment of the patient with resibufagenin.

These and other objects of the invention will be more fully understood from the following description of the invention on reference to the illustrations appended hereto.

DESCRIPTION OF THE PREFERRED EMBODIMENTS

As used herein, the term "patient" refers to members of the animal kingdom including human beings.

The term "body specimen" means a specimen obtained from a patient which contains marinobufagenin and expressly includes blood serum, blood plasma and urine.

As employed herein, a reference to determining the "presence of preeclampsia" shall also be deemed to embrace also a determination of the presence of eclampsia.

The term "substantial elevation" as referred to marinobufagenin concentration as employed herein means an elevation above the normally anticipated range of marinobufagenin in a pregnant person.

Preeclampsia is a disorder generally confined to women who are more than 20 weeks pregnant. It consists in the development of hypertension and proteinuria, generally in the form of albuminuria, and the supervention of excessive edema.

It is currently believed by the present inventor that preeclampsia is another example of volume expansion mediated hypertension differing from that seen in any essential hypertension only in that the kidney is under stress related to the pregnancy. Patients may have a genetic or acquired defect in the ability of their kidneys to excrete a sodium load. This deficiency may not become evident until the patient experiences the stress associated with pregnancy. As they are unable to excrete salt normally they develop volume expansion mediated hypertension. As a result of this deficiency in sodium transport in their kidneys, the salt tends to accumulate thereby causing hypertension and edema. This volume expansion is believed to cause the elaboration of the natriuretic factor known as marinobufagenin, which is employed in the present invention as a marker for diagnosing preeclampsia, as well as being employed in the apparatus and therapeutic method of the present invention.

Marinobufagenin is a cardiotonic steroid which has vasoconstrictor and natruretic properties. Its ability to cause increased sodium excretion is thought to reside in its capability to inhibit the enzyme Na/K ATPase. It is unable to cause the excess sodium to be excreted as a result of the deficiency referred to herein above in the sodium transport pathway.

In preeclampsia, the fluid is mostly in the interstitial space where it has leaked from the intravascular space. It is believed by the present inventor that the circulating factor has a role in this "leakiness" of the vascular tree. The uterine vasculature of the preeclamptic patient is characterized by the failure of the decidual small arterioles to dilate normally thereby resulting in large bore, low resistance channels that nourish the placenta and fetus. Instead, these arterioles remain small diameter, high resistance vessels, a condition that is believed by the present inventor to result from the effects of the circulating factor. The net result is that decreased uteroplacental perfusion occurs causing intrauterine growth restriction, prematurity, and fetal wastage.

Tests performed on rat models of preeclampsia have resulted in the conclusion that marinobufagenin is mildly elevated in normal pregnancy, as the pregnancy is an example of natural volume expansion. It is elevated substantially more in preeclamptic rats. Dissecting of the individual vessels from the preeclamptic rats resulted in the determination that when vessels from normal pregnant animals or rats are perfused with marinobufagenin, they do not constrict, while perfusion of vessels from preeclamptic rats with marinobufagenin results in constriction that averages about 36 percent as compared with the controlled circumstance.

The preferred practice of the present invention for determining the presence of preeclampsia includes determining if there has been a substantial elevation in marinobufagenin concentration of the blood-derived or urine-derived specimen. The base line for such evaluations may be obtained through evaluation of normal pregnant human patients. If such elevation of marinobufagenin does exist, it is concluded that preeclampsia exists. The method provides a method capable of making this determination independently of whether vasoconstriction hypertension or other types of hypertension exist in the patient.

In general, it is preferred that a substantial elevation in marinobufagenin from normal range be deemed to be at least about a 50 percent elevation in marinobufagenin concentration above the limit of the range of normal human patients before it is determined that preeclampsia exists, and preferably an elevation in the range of at least about 100 to 200 percent elevation. This elevation is ascertained by determining the marinobufagenin concentration of the patient's body and comparing it with an established normal specimen range.

The body specimen employed in practicing the method of the present invention may advantageously be urine or a blood-derived specimen, such as blood serum or blood plasma.

Patients with preeclampsia are volume expanded, but the majority of the excess fluid is in the interstitial rather than the intravascular compartment.

It is believed that one of the syndromes of hypertension in pregnancy called preeclampsia represents a disease entity caused by excessive volume expansion. An animal model of preeclampsia in the rat ("Volume expansion as a proximate cause of preeclampsia in a rat model", Ianosi-Irimie M R et al., J Am Soc Nephrol, 13:513A, 2002). In this model, hypertension, proteinuria and intrauterine growth restriction occur and mimic the phenotypic characteristics of mild to moderate preeclampsia ("A rat model of preeclampsia", Ianosi-Irimie M. et al. [submitted for publication]). It is believed by the present inventor that the pathogenetic process in this form of volume expansion-mediated preeclampsia involves the elaboration of a humoral substance which has vasoconstrictive properties ("The possible role of digitalislike factors in pregnancy-induced hypertension", Graves, S W, Hypertension, 10[Suppl I]:I-84, 1987) ("Plasma from women with preeclampsia induces an in vitro alteration in the endothelium-dependent behaviour of myometrial resistance arteries", Haymen R. et al., BJOG, 107(1):108, 2000). In the rat model of preeclampsia employed, the urinary excretion of the humoral substance, marinobufagenin (MBG) is increased ("Neutralization of marinobufagenin normalizes blood pressure in a rat model of preeclampsia", Pridjian G et al., J Soc Gynecol Invest, 11(Suppl):260A, 2004). MBG is a cardiotonic and vasoconstrictive steroidal humoral substance which circulates in the blood of patients with preeclampsia ("Circulating bufodienolide and cardenolide sodium pump inhibitors in preeclampsia", Lopatin D A et al., J Hypertens, 17:1179, 1999).

Experiments performed by the present inventor have demonstrated that MGB plays a significant role in the pathogenesis of the preeclamptic syndrome that have been induced in the rat model ("Neutralization of marinobufagenin normalizes blood pressure in a rat model of preeclampsia", Pridjian G et al., J Soc Gynecol Invest, 11(Suppl):260A, 2004) ("The involvement of marinobufagenin in a rat model of preeclampsia", Vu H. et al. [in preparation]). Resibufagenin (RBG) is an analogue of MGB which in cellular systems has no biological effect. This agent is structurally similar to MGB. It is believed that RBG serves as an antagonist to MBG, probably by displacing MBG from its receptors in a process of competitive inhibition.

Experiment

In order to confirm the effectiveness of RBG, experiments were performed. In the experiment, a group of four pregnant rats was provided with a blood pressure cuff on their tails in order to determine the base line blood pressure as shown in the table. In order to create hypertension, MBG was administered to the rats.

TABLE 1

|  | Baseline BP* | BP after MBG | BP after RBG |
|---|---|---|---|
| Rat #1 | 80 | 125 | 95 |
| Rat #2 | 100 | 130 | 120 |
| Rat #3 | 80 | 115 | 110 |
| Rat #4 | 110 | 135 | 105 |

*BP = blood pressure (mmHg)

A dosage of approximately 7 mg per kg of rat weight with the rats weighing in the range of about 200-250 g was employed daily in order to determine the effectiveness of resibufagenin in the treatment of preeclampsia. The dosage was administered intraperitonially and the rats monitored after about three to four days of treatment. The MBG and RBG were administered in a suitable vehicle such as dimethylsulfoxide (DMSO). It is noted that after treatment with RBG, all of the rats experienced a substantial reduction in blood pressure.

It will generally be preferred in employing the method of treatments in humans to effect the treatment from the time the disorder of preeclampsia is discovered (usually after 20 weeks of gestation) until the time of delivery (usually at approximately 36 weeks). The dosage is preferably administered daily in single or multiple doses.

In general, it is preferred to administer resibufagenin orally or parenterally such as by parenteral injection.

While the present description has focused on the preferred use of resibufagenin, it will be appreciated that other bufadienolide derivatives may be employed in lieu thereof or in combination therewith. The application may also be used with resibufagenin analogues.

It will be appreciated that the present invention provides methods for employing a patient's blood or urine and determining whether preeclampsia exists in the patient, thereby permitting appropriate therapeutic measures to be taken. It is preferred in the present invention once confirmation of the existence of human preeclampsia, to treat the patient with a therapeutically effective dose of resibufagenin The invention also contemplates a method for making such determination and providing therapeutic treatment to a patient as by administering appropriate mediation preferably resibufagenin with the dosage corresponding to the other health considerations regarding the patient and the severity of the preeclampsia volume dependent hypertension and the health of the patient in any other respects.

Whereas particular embodiments of the invention have been described herein for purposes of illustration, it will be evident to those skilled in the art that numerous variations of the details may be made without departing from the invention as defined in the appended claims.

The invention claimed is:

1. A method of treating a human patient for preeclampsia comprising administering to said patient suffering from preeclampsia a therapeutically effective dose of resibufagenin in order to reduce the blood pressure of said patient.

2. The method of claim 1 including
prior to treating said patient confirming the existence of preeclampsia in said patient.

3. The method of claim 2 including
administering said resibufagenin parenterally.

4. The method of claim 2 including
administering said resibufagenin orally.

5. The method of claim 3 including
administering said resibufagenin by parenteral injection.

6. The method of claim 1 including
effecting said treatment daily.

7. The method of claim 1 including
effecting said determination of the existence of human preeclampsia through an elevation in marinobufagenin.

8. The method of claim 6 including
administering said treatment daily in a single daily dose.

9. The method of claim 6 including
effecting said treatment daily in multiple daily doses.

10. The method of claim 6, wherein the method is carried out during the period beginning with the twentieth week of gestation.

11. The method of claim 10 including
continuing said treatment until about the day of delivery.

* * * * *

UNITED STATES PATENT AND TRADEMARK OFFICE
CERTIFICATE OF CORRECTION

| | | |
|---|---|---|
| PATENT NO. | : 7,759,329 B2 | Page 1 of 1 |
| APPLICATION NO. | : 11/577450 | |
| DATED | : July 20, 2010 | |
| INVENTOR(S) | : Jules B. Puschett | |

It is certified that error appears in the above-identified patent and that said Letters Patent is hereby corrected as shown below:

Title page, second column, OTHER PUBLICATIONS, line 7, "biophysical" should read --Biophysical--.
Title page, second column, ABSTRACT, line 12, "in lieu of" should read --in lieu--.
Column 1, line 19, "Preec-" should read --Pre- --.
Column 1, line 20, "lampsia" should read --eclampsia--.
Column 2, line 3, "patent" should read --patient--.
Column 2, line 49, "also be deemed to embrace also" should read --also be deemed to embrace--.
Column 2, line 56, "It consists in the" should read --It consists of the--.
Column 2, line 60, "preec-" should read --pre- --.
Column 2, line 61, "lampsia" should read --eclampsia--.
Column 3, line 1, "normally they" should read --normally, they--.
Column 3, line 7, "preec-" should read --pre- --.
Column 3, line 8, "lampsia" should read --eclampsia--.
Column 3, line 11, "natruetic properties" should read --natriuretic properties--.
Column 3, line 15, "herein above" should read --hereinabove--.
Column 4, line 16, "in vitro" should read --*in vitro*--.
Column 5, line 26, "appropriate mediation" should read --appropriate medication--.

Signed and Sealed this
Eighth Day of February, 2011

David J. Kappos
*Director of the United States Patent and Trademark Office*